(12) United States Patent
Levner et al.

(10) Patent No.: US 11,085,911 B2
(45) Date of Patent: Aug. 10, 2021

(54) FLUIDIC DEVICE FOR QUANTIFYING THE DYNAMIC PERMEABILITY AND HYDRAULIC CONDUCTIVITY OF LIVING TISSUE LAYERS

(71) Applicant: President and Fellows of Harvard College, Cambridge, MA (US)

(72) Inventors: Daniel Levner, Brookline, MA (US); Christopher David Hinojosa, Malden, MA (US); Andries D. van der Meer, Enschede (NL); Marinke van der Helm, Enschede (NL); Abhishek Jain, Roslindale, MA (US); Donald Elliot Ingber, Boston, MA (US); Marjon Zamani, Boston, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 25 days.

(21) Appl. No.: 16/534,255

(22) Filed: Aug. 7, 2019

(65) Prior Publication Data
US 2019/0360994 A1 Nov. 28, 2019

Related U.S. Application Data

(63) Continuation of application No. 15/694,577, filed on Sep. 1, 2017, now abandoned, which is a continuation
(Continued)

(51) Int. Cl.
*G01N 33/483* (2006.01)
*G01N 33/50* (2006.01)
(Continued)

(52) U.S. Cl.
CPC ...... *G01N 33/4833* (2013.01); *B01L 3/50273* (2013.01); *B01L 3/502715* (2013.01);
(Continued)

(58) Field of Classification Search
CPC .................................................. G01N 33/4833
(Continued)

(56) References Cited

U.S. PATENT DOCUMENTS

| 7,122,579 B2 | 10/2006 | Schwartz |
| 2001/0052460 A1 | 12/2001 | Chien |

(Continued)

FOREIGN PATENT DOCUMENTS

| CN | 201 130 182 Y | 10/2008 |
| WO | WO 2016/010861 | 1/2016 |

OTHER PUBLICATIONS

Lyu et al., Measuring transport properties of cell membranes by a PDMS microfluidic device with controllability over changing rate of extracellular solution, 2014, Sensors and Actuators B, 197, pp. 28-34 (Year: 2014).*
(Continued)

*Primary Examiner* — Holly Kipouros
(74) *Attorney, Agent, or Firm* — Nixon Peabody LLP

(57) ABSTRACT

Systems and methods for measuring dynamic hydraulic conductivity and permeability associated with a cell layer are disclosed. Some systems include a microfluidic device, one or more working-fluid reservoirs, and one or more fluid-resistance element. The microfluidic device includes a first microchannel, a second microchannel, and a barrier therebetween. The barrier includes a cell layer adhered thereto. The working fluids are delivered to the microfluidic device. The fluid-resistance elements are coupled to one or more of the fluid paths and provide fluidic resistance to cause a pressure drop across the fluid-resistance elements.
(Continued)

Mass transfer occurs between the first microchannel and the second microchannel, which is indicative of the hydraulic conductivity and/or dynamic permeability associated with the cells.

12 Claims, 7 Drawing Sheets

Related U.S. Application Data of application No. PCT/US2016/021025, filed on Mar. 4, 2016.

(60) Provisional application No. 62/128,383, filed on Mar. 4, 2015.

(51) Int. Cl.
  *B01L 3/00* (2006.01)
  *C12M 1/00* (2006.01)
  *G01N 15/08* (2006.01)
  *G01N 15/00* (2006.01)

(52) U.S. Cl.
  CPC .... *B01L 3/502746* (2013.01); *G01N 15/0826* (2013.01); *G01N 33/50* (2013.01); *G01N 33/5005* (2013.01); *B01L 2300/0654* (2013.01); *B01L 2300/0877* (2013.01); *B01L 2300/0883* (2013.01); *B01L 2400/0457* (2013.01); *B01L 2400/0487* (2013.01); *B01L 2400/082* (2013.01); *B01L 2400/084* (2013.01); *B01L 2400/086* (2013.01); *G01N 2015/0065* (2013.01)

(58) Field of Classification Search
  USPC ........................................................ 435/288.7
  See application file for complete search history.

(56) References Cited

U.S. PATENT DOCUMENTS

| 2006/0199260 | A1  | 9/2006  | Zhang |
| 2011/0027804 | A1  | 2/2011  | Yarmush |
| 2011/0250585 | A1* | 10/2011 | Ingber .................. C12N 5/0696 435/5 |
| 2012/0211373 | A1  | 8/2012  | El-Sayed |
| 2014/0342445 | A1  | 11/2014 | Ingber |

OTHER PUBLICATIONS

Datta, Hydraulic Permeability of Food Tissues, 2007, International Journal of Food Properties, 9:4, pp. 767-780 (Year: 2007).*
Provin et al., A Microfluidic Diffusion Cell for Fast and Easy Percutaneous Absorption Assays, Feb. 28, 2015, Pharmaceutical Research, 32, pp. 2704-2712 (Year: 2015).*
Van der Sandt et al., Assessment of active transport of HIV protease inhibitors in various cell lines and the in vitro blood-brain barrier, 2001, AIDS, vol. 15 No. 4, pp. 483-491. (Year: 2001).*
Inamdar, Analysis and Implementation of the Bilayer Microfluidic Geometry [Thesis], 2011, Massachusetts Institute of Technology (Year: 2011).*
Young et al.; "Technique for Real-Time Measurements of Endothelial Permeability in a Microfluidic Membrane Chip Using Laser-Induced Fluorescence Detection"; Anal. Chem., Feb. 1, 2010, vol. 82, No. 3, pp. 808-816 (9 pages).
International Search Report in corresponding International Application No. PCT/US2016/021025, dated Dec. 27, 2016 (5 pages).
Written Opinion in corresponding International Application No. PCT/US2016/021025, dated Dec. 27, 2016 (11 pages).
H.W. Sill et al., "Shear stress increases hydraulic conductivity of cultured endothelial monolayers," American Journal of Physiology: Heart and Circulatory Physiology, vol. 268, No. 2, Feb. 1995 (Feb. 1995), pp. H535-H543, XP05550966, US, ISSN: 0363-6124, DOI: 10.1152/ajpheart.1995.268.2.H535 (9 pages).
Extended European Search Report in European Patent Application No. 16800433.1, dated Feb. 26, 2019 (11 pages).
Chen, W.J.et al.; "A Microfluidic Device with Hydrodynamic Switching for Transport Property Measurements of Cell Membranes"; CMS pp. 1538-1540; 2010 (3 pages).

* cited by examiner

FLUIDIC DEVICE FOR QUANTIFYING THE DYNAMIC PERMEABILITY AND HYDRAULIC CONDUCTIVITY OF LIVING TISSUE LAYERS

CROSS-REFERENCE TO RELATED APPLICATIONS

This application is continuation of U.S. application Ser. No. 15/694,577, filed Sep. 1, 2017, which is a continuation of International Application No. PCT/US2016/021025, filed Mar. 4, 2016, which claims the benefit of U.S. Provisional Application No. 62/128,383, filed Mar. 4, 2015, each of which is herein incorporated by reference in its entirety.

GOVERNMENT SUPPORT

This invention was made with government support under grant no. W911NF-12-2-0036 awarded by U.S. Department of Defense, Advanced Research Projects Agency. The government has certain rights in the invention.

TECHNICAL FIELD

The present invention relates to cell culture systems and fluidic systems. More specifically, the invention relates to systems that provide for improved characterization of the permeability and hydraulic conductivity of dynamic environments, including systems having biological cell layers.

BACKGROUND

Typical laboratory set-ups for measuring hydraulic conductivity of cell layers are generally based on a modified Transwell assay where the tissue is cultured on a semi-permeable substrate or the membrane of a Transwell insert. Fluid is then supplied to the well and a pressure gradient is created between the two sides of the semi-permeable substrate. The fluid is generally allowed to only flow perpendicularly to the surface of the Transwell membrane. Monitoring the fluid flow rate from the insert compartment to the bottom compartment can be used to quantify a static hydraulic conductivity through the tissue. The pressure gradient can be induced by establishing an air-tight connection between the insert and an open reservoir. When quantifying the flow rate in the system (e.g., by collecting outflow or by tracking a bubble moving through capillary tubing), the hydraulic conductivity of the cultured tissue in a static system can be determined. Unfortunately, in-vivo systems are more dynamic and, thus, not accurately modeled by these set-ups.

Combining the set-ups based on a Transwell membrane with a spinning disc or spinning cone rheometer may allow the tissue be subjected to some shear stresses. Studies using such a combined set-up indicate that subjecting the tissue to shear stresses has an important modulatory effect on hydraulic conductivity of tissue, such as endothelial tissue. However, the combined system prevents certain beneficial features, such as monitoring the cells during the experiment and providing for prolonged experimentation. Moreover, these combined set-ups increase cost and complexity of the experiment due to the need for expensive equipment with a number of moving parts. Most importantly, combined set-ups, such as spinning disk or spinning cone rheometers, produce circular patterns of shear stress. These circular flow patterns do not provide accurate simulation of biological conditions.

Another disadvantage of prior art static and combined set-ups is that they do not incorporate ways to dynamically alter the flow rates and pressure gradients in the system. These parameters can change over time in real-life tissues, and these changes can have important roles in physiological processes that involve changes in hydraulic conductivity. For example, when a blood vessel ruptures, the hydraulic conductivity of the vessel wall is increased for only a brief time. Within minutes, the local pressure gradient is decreased by vasospasm and the hydraulic conductivity of the ruptured wall is lowered by blood clotting.

Additionally, the permeability of biological tissues for specific substances or particles is an important parameter in fields like drug discovery, toxicology, and physiology. For example, the extent that a substance can permeate specific tissues determines important aspects of the substance's pharmacokinetics and toxic risk profile. Additionally, the proper functioning of tissues can be probed by testing their permeability to standard tracer molecules. These tracer molecules can include relatively inert compounds such as dextran, inulin, and polyethylene glycol, or biologically active compounds such as glucose.

Typical laboratory setups for measuring permeability of cell layers are generally based on modified Transwell assays where tissue is cultured on a semi-permeable substrate or the membrane of a Transwell insert. The insert is filled with medium including the substance of interest and then placed in a well that has been filled with control medium. The height of the media in the insert and the well are matched to prevent convective transport through the tissue driven by hydrostatic pressure. By repetitively taking samples from the well, the rate at which a substance diffuses through the tissue can be determined. After normalizing for the concentration gradient and the surface area, this rate of diffusion is defined as the permeability coefficient of that particular substance for that particular tissue.

Attempts have been made to produce dynamic assays for measuring permeability of cell layers through use of microfluidic devices. These dynamic assays rely on the same principles as described above by employing two compartments separated by a semi-permeable barrier that is covered by tissue. However, the media in the compartments is moving through the microfluidic device in the dynamic version of the assay. This flow of media is needed to maintain a stable concentration gradient over the cultured tissue. Unfortunately, the volumes of the microfluidic compartments are so low that even small absolute amounts of media transferred through the tissue can dramatically affect the measurement of concentrations in the system.

A major challenge when performing dynamic permeability assays in microfluidic systems is to avoid convective transport between the two compartments. Even small differences in the fluidic resistance between the two compartments can drive a cross-flow from one compartment to the other. Differences in fluidic resistance may be a result of the design of the microfluidic device or experimental setup, such as different hydraulic diameters for the two compartments, different downstream lengths of the two compartments, or inherent differences due to manufacturing tolerances. Further, differences in fluidic resistance can also arise during operation of the systems such as when a channel is blocked with small pieces of dirt, clumps of tissue, or small air bubbles. These small differences make it very difficult, if not impossible, to standardize the results of the assay because transport is driven by both diffusion and convection. This also makes it difficult, if not impossible, to compare the results from the dynamic assay with results from conventional Transwell studies, or to model whole tissues and organs in vivo.

The present invention solves many of the problems associated with the prior art systems by providing new systems and methods for quantifying the dynamic hydraulic conductivity and the dynamic permeability of cell layers by use of fluidic and microfluidic devices having the cell layers located therein.

SUMMARY

According to aspects of the present invention, a system for measuring dynamic hydraulic conductivity associated with a cell layer includes a microfluidic device, a working-fluid reservoir, a first fluid line, a flow-determining element, and a second fluid line. The microfluidic device includes a first microchannel, a second microchannel, and a barrier located at an interface region between the first microchannel and the second microchannel. The barrier includes a first side facing toward the first microchannel and a second side facing toward the second microchannel. The first side has the cell layer adhered thereto. The working-fluid reservoir includes a working fluid that is delivered to the first microchannel. The first fluid line is for delivering a first portion of a working fluid from the first microchannel to a first fluid reservoir. The flow-determining element is coupled to the first fluid line and is configured to determine flow of fluid therethrough. The second fluid line is for delivering a second portion of the working fluid from the second microchannel to a second fluid reservoir. The second portion of the working fluid moves from the first microchannel to the second microchannel through the cell layer and is indicative of the dynamic hydraulic conductivity associated with the cells.

According to further aspects of the present invention, a method for measuring dynamic hydraulic conductivity associated with cells includes flowing a working fluid through a first microchannel, applying a first pressure to the working fluid in the first microchannel, collecting a first portion of the working fluid exiting the first microchannel, collecting the second portion of the working fluid exiting the second microchannel, and calculating a dynamic hydraulic conductivity of the layer of cells. The working fluid is flowed through the first microchannel at a first flow rate along a layer of cells. The layer of cells is disposed on a barrier. The first flow rate causes a first shear stress on the layer of cells. The first pressure is applied to the working fluid in the first microchannel to cause a second portion of the working fluid to travel to a second microchannel through the layer of cells and the barrier. The calculating of the dynamic hydraulic conductivity of the layer of cells is based on the first pressure and the second portion.

According to still further aspects of the present invention, a method for measuring dynamic hydraulic conductivity associated with cells includes moving a working fluid through a first microchannel of a microfluidic device, measuring a first portion of the working fluid that exits the first microchannel, measuring a second portion of the working fluid that migrates through the cell layer and a barrier and exits a second microchannel of the microfluidic device, and determining the dynamic hydraulic conductivity of the cells based on at least one of the first portion and the second portion of the working fluids.

According to yet further aspects of the present invention, a system for measuring dynamic hydraulic conductivity associated with cells includes a microfluidic device, a first fluid path, and a second fluid path. The microfluidic device has a first microchannel, a second microchannel, and a barrier located at an interface region between the first microchannel and the second microchannel. The barrier includes a first side facing toward the first microchannel and a second side facing toward the second microchannel. At least one of the first side and the second side has a cell layer adhered thereto. The first fluid path is associated with the first microchannel. The first fluid path is for delivering a fluid to and from the first microchannel. The first fluid path includes a flow-determining element downstream from the first microchannel to maintain a substantially constant fluid pressure along the cell layer adhered to the barrier. The second fluid path is associated with the second microchannel. The second fluid path is for delivering, from the second microchannel, the fluid that has migrated through the barrier and the cell layer. The flow rate of the fluid that is delivered from the second microchannel is indicative of the dynamic hydraulic conductivity associated with the cell layer.

According to still yet further aspects of the present invention, a system for measuring dynamic permeability of a cell layer includes a microfluidic device, a first working-fluid reservoir, a first fluid line, a first fluid-resistance element, a second working-fluid reservoir, a second fluid line, and a second fluid-resistance element. The microfluidic device includes a first microchannel, a second microchannel, and a barrier located at an interface region between the first microchannel and the second microchannel. The barrier includes a first side facing toward the first microchannel and a second side facing toward the second microchannel. The first side includes the cell layer adhered thereto. The first working-fluid reservoir contains a first working fluid that is delivered to the first microchannel. The first fluid line delivers fluid from the first microchannel to a first output-fluid reservoir. The first fluid-resistance element is coupled to the first fluid line. The first fluid-resistance element has a first fluidic resistance that causes a pressure drop across the first fluid-resistance element. The second working-fluid reservoir contains a second working fluid that is delivered to the second microchannel. The second fluid line delivers fluid from the second microchannel to a second output-fluid reservoir. The second fluid-resistance element is coupled to the second fluid line. The second fluid-resistance element has a second fluidic resistance that causes a pressure drop across the second fluid-resistance element. The first fluidic resistance and the second fluidic resistance are substantially larger than the nominal resistances of the first and the second microchannel, respectively, so as to inhibit convective flow between the first working fluid and the second working fluid through the barrier and the cell layer, thereby allowing measurement of dynamic permeability through the cell layer.

According to additional aspects of the present invention, a method for measuring dynamic permeability of a cell layer includes the acts of moving a first working fluid through a first fluid path, moving a second working fluid through a second fluid path, and measuring an analyte in the second working fluid. The first fluid path includes a first microchannel of a microfluidic device and a first fluid-resistance element. The microfluidic device further includes a second microchannel and a barrier located at an interface region between the first microchannel and the second microchannel. The barrier includes a first side facing toward the first microchannel and has the cells adhered thereto. The first fluid-resistance element has a first fluidic resistance that causes a pressure drop across the first fluid-resistance element. The first working fluid includes the analyte. The second fluid path includes the second microchannel of the microfluidic device and a second fluid-resistance element. The second fluid-resistance element has a second fluidic resistance that causes a pressure drop across the second fluid-resistance element. The measuring the analyte in the second working fluid occurs after the second working fluid has passed through the second microchannel. The measured analyte is indicative of the dynamic permeability of the cell layer.

According to yet additional aspects of the present invention, a system for measuring dynamic permeability of a cell layer includes a microfluidic device, a first working-fluid reservoir, a first fluid line, a first fluid-resistance element, a second working-fluid reservoir, a second fluid line, and a second fluid-resistance element. The microfluidic device includes a first microchannel, a second microchannel, and a barrier located at an interface region between the first microchannel and the second microchannel. The barrier includes a first side facing toward the first microchannel and a second side facing toward the second microchannel. The first side has the cell layer adhered thereto. The first working-fluid reservoir contains a first working fluid that is delivered to the first microchannel. The first fluid line delivers fluid away from the first microchannel. The first fluid-resistance element is coupled to the first fluid line. The first fluid-resistance element includes a first fluidic resistance that is substantially larger than the nominal resistance of the first microchannel. The second working-fluid reservoir contains a second working fluid that is delivered to the second microchannel. The second fluid line delivers fluid away from the second microchannel. The second fluid-resistance element is coupled to the second fluid line. The second fluid-resistance element has a second fluidic resistance that is substantially larger than the nominal resistance of the second microchannel. The first fluidic resistance and the second fluidic resistance create a negligible pressure drop across the barrier and the cell layer while the first working fluid and the second working fluid flow through the system, thereby allowing the measurement of dynamic permeability through the barrier and the cell layer.

According to aspects of the present invention, a system for measuring dynamic hydraulic conductivity associated with a cell layer includes a fluidic device, a working-fluid reservoir, a first fluid line, a flow-determining element, and a second fluid line. The fluidic device includes a first channel, a second channel, and a barrier located at an interface region between the first channel and the second channel. The barrier includes a first side facing toward the first channel and a second side facing toward the second channel. The first side has the cell layer adhered thereto. The working-fluid reservoir includes a working fluid that is delivered to the first channel. The first fluid line is for delivering a first portion of a working fluid from the first channel to a first fluid reservoir. The flow-determining element is coupled to the first fluid line and is configured to determine flow of fluid therethrough. The second fluid line is for delivering a second portion of the working fluid from the second channel to a second fluid reservoir. The second portion of the working fluid moves from the first channel to the second channel through the cell layer and is indicative of the dynamic hydraulic conductivity associated with the cells.

According to further aspects of the present invention, a method for measuring dynamic hydraulic conductivity associated with cells includes flowing a working fluid through a first channel, applying a first pressure to the working fluid in the first channel, collecting a first portion of the working fluid exiting the first channel, collecting the second portion of the working fluid exiting the second channel, and calculating a dynamic hydraulic conductivity of the layer of cells. The working fluid is flowed through the first channel at a first flow rate along a layer of cells. The layer of cells is disposed on a barrier. The first flow rate causes a first shear stress on the layer of cells. The first pressure is applied to the working fluid in the first channel to cause a second portion of the working fluid to travel to a second channel through the layer of cells and the barrier. The calculating of the dynamic hydraulic conductivity of the layer of cells is based on the first pressure and the second portion.

According to still further aspects of the present invention, a method for measuring dynamic hydraulic conductivity associated with cells includes moving a working fluid through a first channel of a fluidic device, measuring a first portion of the working fluid that exits the first channel, measuring a second portion of the working fluid that migrates through the cell layer and a barrier and exits a second channel of the fluidic device, and determining the dynamic hydraulic conductivity of the cells based on at least one of the first portion and the second portion of the working fluids.

According to yet further aspects of the present invention, a system for measuring dynamic hydraulic conductivity associated with cells includes a fluidic device, a first fluid path, and a second fluid path. The fluidic device has a first channel, a second channel, and a barrier located at an interface region between the first channel and the second channel. The barrier includes a first side facing toward the first channel and a second side facing toward the second channel. At least one of the first side and the second side has a cell layer adhered thereto. The first fluid path is associated with the first channel. The first fluid path is for delivering a fluid to and from the first channel. The first fluid path includes a flow-determining element downstream from the first channel to maintain a substantially constant fluid pressure along the cell layer adhered to the barrier. The second fluid path is associated with the second channel. The second fluid path is for delivering, from the second channel, the fluid that has migrated through the barrier and the cell layer. The flow rate of the fluid that is delivered from the second channel is indicative of the dynamic hydraulic conductivity associated with the cell layer.

According to still yet further aspects of the present invention, a system for measuring dynamic permeability of a cell layer includes a fluidic device, a first working-fluid reservoir, a first fluid line, a first fluid-resistance element, a second working-fluid reservoir, a second fluid line, and a second fluid-resistance element. The fluidic device includes a first channel, a second channel, and a barrier located at an interface region between the first channel and the second channel. The barrier includes a first side facing toward the first channel and a second side facing toward the second channel. The first side includes the cell layer adhered thereto. The first working-fluid reservoir contains a first working fluid that is delivered to the first channel. The first fluid line delivers fluid from the first channel to a first output-fluid reservoir. The first fluid-resistance element is coupled to the first fluid line. The first fluid-resistance element has a first fluidic resistance that causes a pressure drop across the first fluid-resistance element. The second working-fluid reservoir contains a second working fluid that is delivered to the second channel. The second fluid line delivers fluid from the second channel to a second output-fluid reservoir. The second fluid-resistance element is coupled to the second fluid line. The second fluid-resistance element has a second fluidic resistance that causes a pressure drop across the second fluid-resistance element. The first fluidic resistance and the second fluidic resistance are substantially larger than the nominal resistances of the first and the second channel, respectively, so as to inhibit convective flow between the first working fluid and the second working fluid through the barrier and the cell layer, thereby allowing measurement of dynamic permeability through the cell layer.

According to additional aspects of the present invention, a method for measuring dynamic permeability of a cell layer includes the acts of moving a first working fluid through a first fluid path, moving a second working fluid through a second fluid path, and measuring an analyte in the second working fluid. The first fluid path includes a first channel of a fluidic device and a first fluid-resistance element. The fluidic device further includes a second channel and a barrier located at an interface region between the first channel and the second channel. The barrier includes a first side facing toward the first channel and has the cells adhered thereto. The first fluid-resistance element has a first fluidic resistance that causes a pressure drop across the first fluid-resistance element. The first working fluid includes the analyte. The second fluid path includes the second channel of the fluidic device and a second fluid-resistance element. The second fluid-resistance element has a second fluidic resistance that causes a pressure drop across the second fluid-resistance element. The measuring the analyte in the second working fluid occurs after the second working fluid has passed through the second channel. The measured analyte is indicative of the dynamic permeability of the cell layer.

According to yet additional aspects of the present invention, a system for measuring dynamic permeability of a cell layer includes a fluidic device, a first working-fluid reservoir, a first fluid line, a first fluid-resistance element, a second working-fluid reservoir, a second fluid line, and a second fluid-resistance element. The fluidic device includes a first channel, a second channel, and a barrier located at an interface region between the first channel and the second channel. The barrier includes a first side facing toward the first channel and a second side facing toward the second channel. The first side has the cell layer adhered thereto. The first working-fluid reservoir contains a first working fluid that is delivered to the first channel. The first fluid line delivers fluid away from the first channel. The first fluid-resistance element is coupled to the first fluid line. The first fluid-resistance element includes a first fluidic resistance that is substantially larger than the nominal resistance of the first channel. The second working-fluid reservoir contains a second working fluid that is delivered to the second channel. The second fluid line delivers fluid away from the second channel. The second fluid-resistance element is coupled to the second fluid line. The second fluid-resistance element has a second fluidic resistance that is substantially larger than the nominal resistance of the second channel. The first fluidic resistance and the second fluidic resistance create a negligible pressure drop across the barrier and the cell layer while the first working fluid and the second working fluid flow through the system, thereby allowing the measurement of dynamic permeability through the barrier and the cell layer.

These and other capabilities of the invention, along with the invention itself, will be more fully understood after a review of the following figures, detailed description, and claims.

BRIEF DESCRIPTION OF THE DRAWINGS

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Figure 1:
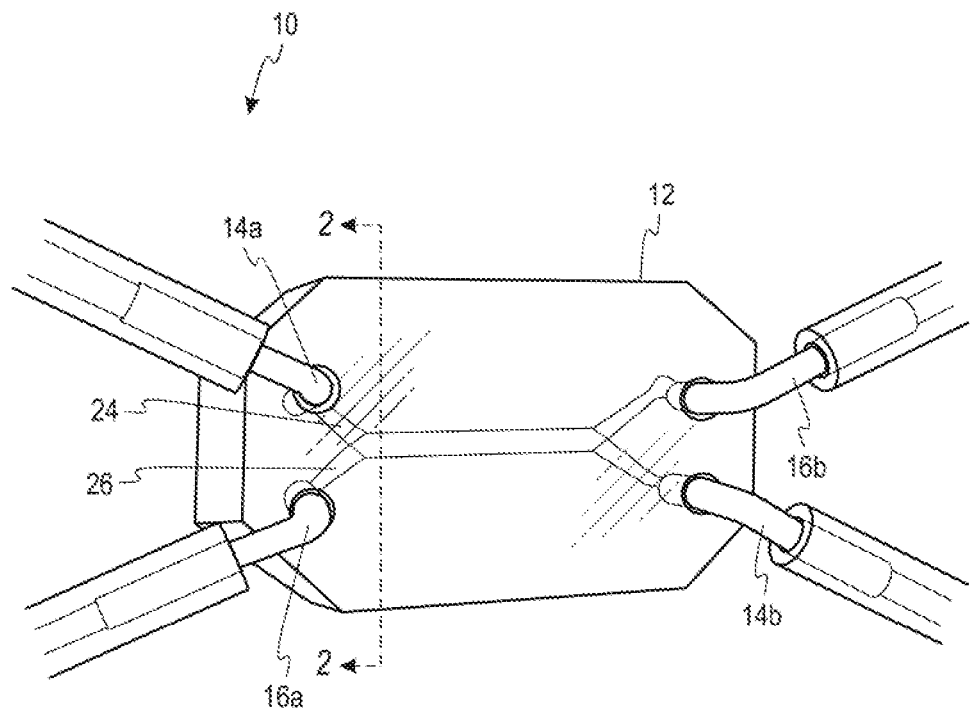
FIG. 1 illustrates an exemplary organ-on-chip device that may be used with systems of the present invention.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The bulk flow or convective transfer of fluids between different compartments in the human body is determined by pressure gradients and the hydraulic conductivity of the tissue between the compartments. Hydraulic conductivity is a quantification of the rate at which a fluid such as water flows through a layer of tissue. Hydraulic conductivity is given as the volumetric flow rate divided by the area and pressure difference. Some physiological examples of fluid flow between different compartments in the body are the filtration of blood in the capillaries, the interstitial flow through three-dimensional compartments like cartilage and other tissues, the filtration of blood in the glomeruli of the kidney, and the filtration of blood in the choroid plexus and the cerebral capillaries to generate cerebrospinal fluid.

Diffusive or quasi-diffusive transfer of fluids or components of fluids between different compartments in the human body is determined by the permeability of the tissues. The permeability of the cell layer differs depending on a variety of factors such as the analyte being studied, the concentration gradient across the cell layer, the surface area of the cell layer, the shear forces on the surface of the cell layer, the state of the cell layer, the capability of the cell layer to actively transport or pump back the analyte, etc. Some in-vivo examples of permeability of the cell layer include transfer and accumulation of toxic compounds, pharmacological compounds, physiological compounds, or the like.

Some, if not all, tissues can sense fluid flow running through or along them and can have a physiologically relevant response to it. Additionally, alterations in the hydraulic conductivity of tissues are involved in many pathological states. For example, inflammation in tissues can lead to endothelial or epithelial increases in hydraulic conductivity. These changes are intimately linked to pathological processes like hemorrhage and proteinuria. In three-dimensional tissues like cartilage and bone, inflammation can lead to changes in the hydraulic conductivity, which can cause, for example, joint stiffening.

In order to model physiological and pathological processes, and to determine the hydraulic conductivity and permeability of specific tissues and cell layers, in-vitro modeling is an indispensable tool. The present invention relates to fluidic devices, systems, and methods that provide for determining hydraulic conductivity and permeability of tissues under dynamic conditions. Fluidic devices, systems, and methods in accord with the present invention allow for many benefits over existing systems, such as more accurate modeling of physical systems. More specifically, fluidic devices, systems, and methods disclosed herein can subject tissues and cell cultures to dynamic conditions that more closely simulate living systems. For example, fluidic devices, systems, and methods as disclosed herein can produce non-circular shear stresses across exposed surfaces of the tissues and cultured cell layers, and can produce physiologically relevant flow patterns such as laminar flow, turbulent flow, pulsating flow, and the like. The incorporation of physiologically relevant flow over the surface of a cell layer while monitoring its hydraulic conductivity and permeability increases the realism, versatility, and physiological relevance of the set-up. Moreover, fluidic devices, systems, and methods as disclosed herein can provide for monitoring dynamic hydraulic conductivity and dynamic permeability changes in real-time.

Further, embodiments of the present invention provide for increased accuracy of physiological models because conditions such as flow rates, pressure gradients, and supplied analyte concentrations can be varied while using the same tissue or cultured cell layer without disturbing the cells, thus providing more accurate characterization by inhibiting the effects of batch-to-batch inconsistency. The present invention also provides for altering pressure gradients, flow rates, and/or supplied analyte concentrations in a simple, straight-forward way by simply changing or modifying one or more downstream flow-determining elements, as will be described in more detail below.

Yet further, embodiments of the present invention provide for systems and methods that are more robust by reducing or eliminating the need for moving parts, and allow for use of various analytical or image-gathering techniques, such as spectroscopy and microscopy on cells in real time as the experiment proceeds. Additionally, the present invention may allow for hydraulic conductivity of the same cells to be measured over the course of hours, days, weeks, etc.

Still yet further, embodiments of the present invention provide for systems and methods that are more robust and allow for long-term consistency in the testing procedure. For example, fluidic-resistance elements can be used to inhibit flow differences caused by blockages, such as small pieces of dirt, clumps of tissue, or small air bubbles. This allows for precise measurement of permeability coefficients even in systems that have an inherent or unwanted difference in fluidic resistance between the two fluidic compartments. Further, it allows for data collection over a longer period of where the occurrence of such blockages is generally unavoidable.

The functionality of cells and tissue types (and even organs) can be implemented in one or more microfluidic devices or "chips" that enable researchers to study these cells and tissue types outside of the body while mimicking much of the stimuli and environment that the tissue is exposed to in-vivo. It can also be desirable to implement these microfluidic devices into interconnected components that can simulate groups of organs or tissue systems. Preferably, the microfluidic devices can be easily inserted and removed from an underlying fluidic system that connects to these devices in order to vary the simulated in-vivo conditions and organ systems.

Figure 2:
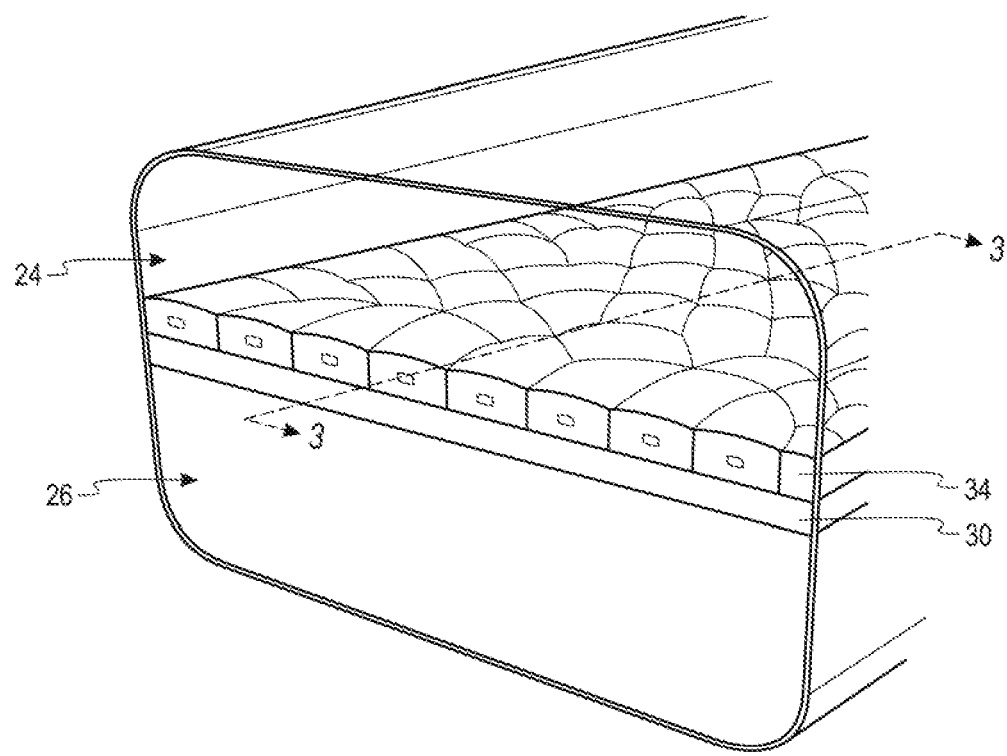
FIG. 2 is a cross-section of the organ-on-chip device taken along line 2-2 of FIG. 1, illustrating the first and second microchannel of the organ-on-chip device.

FIGS. 1 and 2 illustrate one type of an organ-on-chip ("OOC") device 10. The OOC device 10 includes a body 12 that is typically made of a polymeric material. The body 12 includes a first fluid inlet 14a and a first fluid outlet 14b. The body 12 further includes a second fluid inlet 16a and a second fluid outlet 16b. The first fluid inlet 14a and the first fluid outlet 14b allow fluid flow through a first microchannel 24. The second fluid inlet 16a and the second fluid outlet 16b allow fluid flow through a second microchannel 26. The first microchannel 24 is separated from the second microchannel 26 by a barrier 30. The barrier 30 may be any suitable semi-permeable barrier that permits migration of cells, particulates, media, proteins, and/or chemicals between the first microchannel 24 and the second microchannel 26. For example, the barrier 30 can include gels, layers of different tissue, arrays of micro-pillars, membranes, combinations thereof, and the like. Depending on the application, the barrier 30 may have openings or pores to permit the migration of cells, particulates, media, proteins, and/or chemicals between the first microchannel 24 and the second microchannel 26. In some preferred embodiments, the barrier 30 is a porous membrane that includes a cell layer 34 disposed on at least a first surface of the membrane.

While the illustrated embodiment includes only a single cell layer 34, the barrier 30 may include more than a single cell layer 34 disposed thereon. For example, the barrier 30 can include the cell layer 34 disposed within the first microchannel 24, the second microchannel 26, or each of the first and second microchannels 24, 26. Additionally or alternatively, the barrier 30 can include a first cell layer 34 disposed within the first microchannel 24 and a second cell layer within the second microchannel 26. Additionally or alternatively, the barrier 30 can include a first cell layer 34 and a second cell layer disposed within the first microchannel 24, the second microchannel 26, or each of the first and second microchannels 24, 26. Extracellular matrix gels can be used in addition to or instead of the cell layers. Beneficially, these various combinations provide for in-vitro modeling of various cells, tissues, and organs including three-dimensional structures and tissue-tissue interfaces such as brain astrocytes, kidney glomuralar epithelial cells, etc. In one embodiment of the OOC device 10, the first and second microchannels 24, 26 generally have a length of less than about 2 cm, a height of less than 200 µm, and a width of less than 400 µm. More details on the OOC device 10 can be found in, for example, U.S. Pat. No. 8,647,861, which is owned by the assignee of the present application and is incorporated by reference in its entirety.

The OOC device 10 is configured to simulate a biological function associated with cells, such as simulated organs, tissues, etc. One or more properties of a working fluid may change as the working fluid is passed through the microchannels 24, 26 of the OOC device 10, producing an effluent. As such, the effluent is still a part of the working fluid, but its properties and/or constituents may change when passing through the OOC device 10.

The OOC device 10 preferably includes an optical window that permits viewing of the fluid as it moves across the cell layer 34 and the barrier 30. Various image-gathering techniques, such as spectroscopy and microscopy, can be used to quantify and evaluate the fluid flow or analyte flow through the cell layer 34 and the effect of shear on the cell layer 34 that is caused by different flow rates across the cell layer 34.

Figure 3:
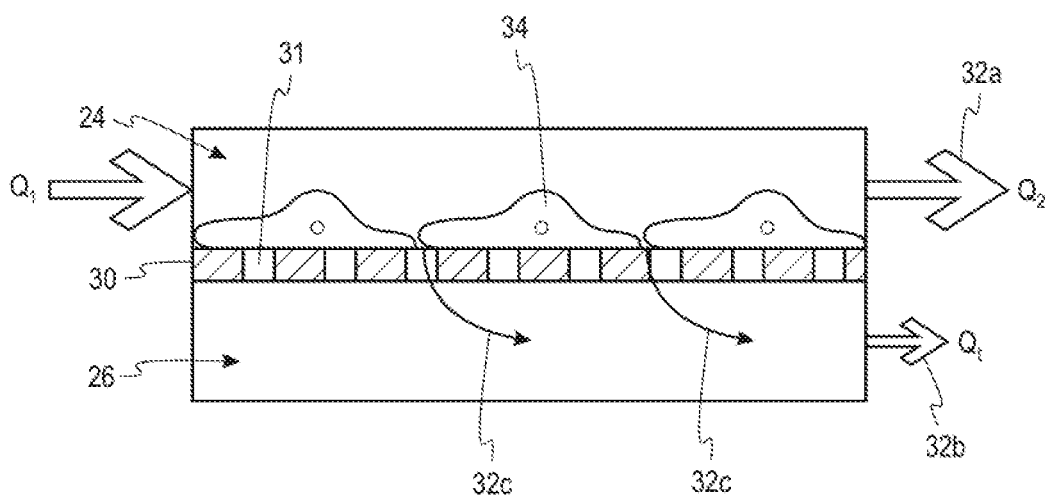
FIG. 3 is a cross-section of the organ-on-chip device taken along line 3-3 of FIG. 2, illustrating fluid flow between the first microchannel and the second microchannel of the organ-on-chip device of FIG. 1.

FIG. 3 schematically illustrates a cross-sectional view of the OOC device 10 across the length of the first and second microchannels 24, 26 along line 3-3 in FIG. 2. The barrier 30 includes pores 31, which can have various dimensions based on the barrier 30 that is chosen. In the illustrated example, a cell layer 34 is disposed within the first microchannel 24 and on the first upper surface of the barrier 30. Fluid enters the first microchannel 24 and flows from the inlet toward the outlet of the first microchannel 24. As the fluid flows from the inlet toward the outlet of the first microchannel 24, contact between the fluid and the surface of the cells 34 exerts a shear stress on the cells 34. This shear stress can deform the individual cells 34, or affect other changes in the physical or biological properties of the cells 34.

In some embodiments for quantifying the hydraulic conductivity of biological cell layers, there is no fluid that enters the second fluid inlet 16a of the second microchannel 26 such that the only fluid entering the OOC device 10 is from the first fluid inlet 14a. In some embodiments, the second microchannel 26 is filled with the fluid at the initiation of the hydraulic testing such that the hydraulic conductivity can be measured contemporaneously with the start of the experiment. In other embodiments, the second microchannel 26 is devoid of fluids at the initiation of the hydraulic testing, and the fluid collected is only fluid that has traversed the barrier 30 during testing. Beneficially, these embodiments provide for simplified measurements of hydraulic conductivity because fewer variables are involved in the test (e.g., instantaneous flow rate through the microchannels, instantaneous pressure within the microchannels, etc.) to determine the hydraulic conductivity.

In some embodiments for quantifying the hydraulic conductivity of biological cell layers, fluid is supplied to the second fluid inlet 16a using a constant-flow element. The constant flow element can be, for example, a volumetric pump or a reservoir having fluid at a generally constant height above the OOC device 10. The constant-flow element is configured to provide a low flow rate to the second fluid inlet 16a such that no significant pressure is generated in the lower channel and the pressure gradient between the first microchannel 24 and the second microchannel 26 is maintained. The hydraulic conductivity can then be quantified by measuring the collected fluid and analyzing the increase in flow rate out of the second microchannel 26.

In some embodiments for testing the hydraulic conductivity of a cell layer, the fluid flows through the first microchannel 24 at a higher pressure than fluid in the second microchannel 26. This creates a pressure gradient ΔP across the barrier 30. If the pressure is sufficiently large, the fluid will travel from the first microchannel 24 to the second microchannel 26 through the cell layer 34 and the pores 31 of the barrier 30, shown by arrows 32c. The fluid that has traversed the cell layer 34 and the barrier 30, exits the second microchannel with a flow rate $Q_t$ as shown by arrow 32b. Because no other fluid has entered the system, the sum of the flow rates out of the flow rates out of the first microchannel $Q_1$ and the second microchannel $Q_t$ will equal the flow rate into the first microchannel $Q_1$. That is, $Q_1=Q_2+Q_t$.

In some embodiments for testing the hydraulic conductivity of the cell layer, fluid flows through the first microchannel 24 at the same pressure as fluid flowing through the second microchannel 26. This inhibits convective flow across the cell layer. However, the cell layer may still transfer fluid between the first microchannel 24 and the second microchannel 26 through active transport processes (e.g., hydraulic pumping). Accordingly, this transport can still be measured under dynamic conditions, and the hydraulic conductivity due to hydraulic pumping can be measured at a variety of flow rates.

The hydraulic conductivity K of the cell layer 34 and the barrier 30 at a predetermined flow rate $Q_1$ of media input to the first microchannel 24 can be quantified by normalizing for the area A of the cell layer 34 using the following equation:

$$K = \frac{Q_T}{A\Delta P}$$

Beneficially, the hydraulic conductivity of individual cell layers $K_L$ can be determined by, for example, accounting for the hydraulic conductivity of the barrier $K_M$. In other words, by knowing the hydraulic conductivity K of the system via the equation above and the hydraulic conductivity of the barrier $K_M$, the hydraulic conductivity of individual cell layers $K_L$ can be derived. Moreover, the hydraulic conductivity of the barrier $K_M$ or fluidic resistance of the barrier can change dependent on the working fluid supplied. Alternatively, it may be possible to select a barrier 30 that is sufficiently porous so as to generally not inhibit flow of media between the first microchannel 24 and the second microchannel 26 relative to the cell layer 34. Similarly, if multiple cell layers 34 or multiple types of cells are co-cultured within the OOC device 10, the conductivity of each layer or cell type can be determined by accounting for the known hydraulic conductivities of the other cell layers 34 or cell types.

Additionally, hydraulic conductivity as a function of shear forces applied to the cells can be determined. For example, hydraulic conductivity may increase in a non-linear fashion, or may increase in step fashion based on applied shear. For example, cells, such a vascular endothelial cells, exhibit a threshold-based response where conductivity of the cell layer is increased in response to a step-increase in luminal shear.

As discussed in more detail below, systems and methods in accord with the present invention can provide for independent control of the flow rate $Q_1$ into the first microchannel 24 and the pressure differential ΔP between the first and the second microchannels 24, 26. Beneficially, these systems provide for more accurate determinations of the in-vivo hydraulic conductivity of individual cell layers.

Figure 4:
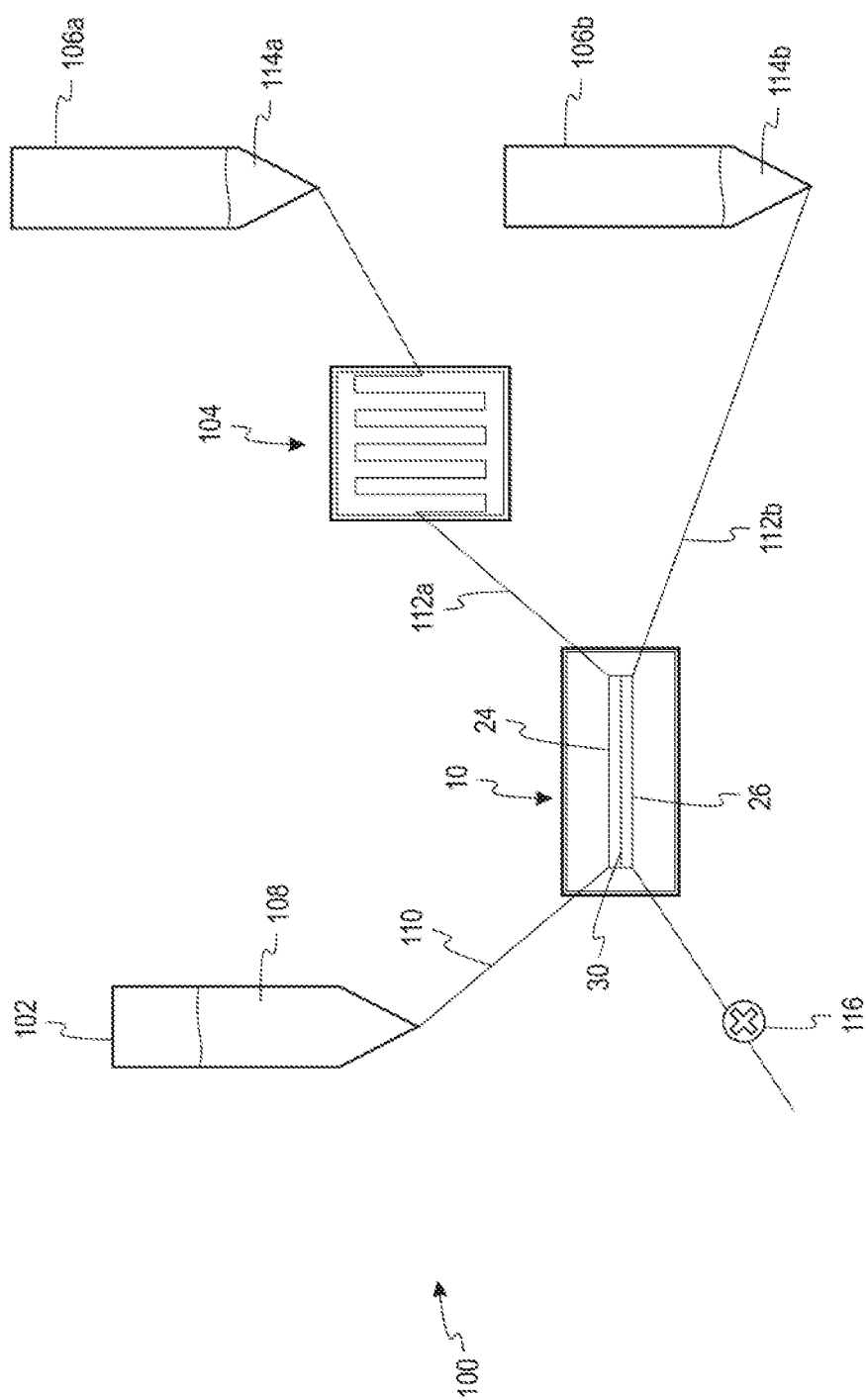
FIG. 4 illustrates a schematic representation of a system for quantifying the dynamic hydraulic conductivity of biological cell layers, according to aspects of the present invention.

Referring now to FIG. 4, a schematic representation of a system 100 for quantifying the hydraulic conductivity of biological cell layers 34 is shown according to aspects of the present invention. The system 100 includes a working-fluid reservoir 102, an OOC device 10, a flow determining element such as fluid-resistance element 104, a first output-fluid reservoir 106a, and a second output-fluid reservoir 106b. The first input 14a (FIG. 1) of the first microchannel 24 of the OOC device 10 is fluidically coupled to the working-fluid reservoir 102. The first output 14b (FIG. 1) of the first microchannel 24 of the OOC device 10 is fluidically coupled to the first output-fluid reservoir 106a. The second input 16a (FIG. 1) for the second microchannel 26 of the OOC device 10 is plugged by stopper 116 to inhibit flow through the second microchannel 26. The second microchannel 26 of the OOC device 10 is fluidically coupled to the second output-fluid reservoir 106b.

The working-fluid reservoir 102 contains a working fluid 108 to be passed through the system 100. In some embodiments, the working fluid 108 is water to determine a baseline or normalized hydraulic conductivity value for the cells or tissue that is a function of water. In some embodiments, the working fluid 108 may be a liquid medium including suspensions or mixtures of cells, particulates, proteins, chemicals, combinations thereof, or the like. In some embodiments, the working fluid 108 may expose the cells of the OOC device 10 to a contaminant, pollutant, or pharmaceutical to determine the how the cells react to such exposure. The working-fluid reservoir 102 is coupled to the first microchannel 24 of the OOC device 10 using input line 110.

The first output-fluid reservoir 106a is coupled to the output of the first microchannel 24 of the OOC device 10 using a first output line 112a. The first output-fluid reservoir 106a collects a first output fluid 114a that has passed through the first microchannel 24 of the OOC device 10. The second output-fluid reservoir 106b is coupled to the output of the second microchannel 26 of the OOC device 10 using a second output line 112b. The second output-fluid reservoir 106b collects a second output fluid 114b that has passed through the second microchannel 26 of the OOC device 10 by migration through the barrier 30 having cells thereon. As will be described in further detail below, the output-fluid reservoirs 106a, 106b can be used to monitor the flow rate through each microchannel 24, 26 and can allow for sampling of the fluid for chemical analysis, molecular analysis, cellular analysis, combinations thereof, and the like.

The flow-determining element is coupled to a fluid path such as the fluid path and associated with the first microchannel 24. The flow-determining element is configured to determine flow of fluid through the fluid path. Beneficially, use of the flow-determining element provides for modularity of the system because flow through the fluid path can be controlled to accommodate differing operating conditions of the OOC device 10, working-fluid reservoir 102, and output-fluid reservoirs 106a, 106b. In some embodiments, the flow-determining element is a pump such as a syringe pump. The pump can be disposed downstream of the first microchannel 24 to determine flow of fluid through the first microchannel 24. In some aspects, the syringe pump draws in fluid from the fluid path to create a generally constant flow of fluid. In some aspects, the syringe pump is coupled to an output-fluid reservoir 106a,b and draws in gas from the output-fluid reservoir 106a,b. The drawing in of gas thereby draws fluid from the fluid path into the output-fluid reservoir 106a,b. In some embodiments, the flow-determining element is a fluid-resistance element 104.

The fluid-resistance element 104 is included in the flow path between the first microchannel 24 of the OOC device 10 and the first output-fluid reservoir 106a. The fluid-resistance element 104 provides a backpressure to the first microfluidic channel 24 by providing a predetermined fluidic resistance to the fluid path associated with the first microchannel 24. The fluidic resistance results in a pressure drop or head loss across the fluid-resistance element 104. Beneficially, use of the fluid-resistance element 104 provides for modularity of the system 100 because a plurality of fluid-resistance elements 104 having different fluidic resistances can be used to accommodate differing operating conditions of the OOC device 10, working-fluid reservoir 102, and output-fluid reservoirs 106a, 106b. Additionally, the plurality of fluid-resistance elements 104 can be coupled in series and/or parallel to provide for fluidic resistances that are different from the predetermined fluidic resistances of the individual fluid-resistance elements 104. The fluid-resistance elements 104 can be, for example, a channeled resistor or a tubular resistor, such as those described in U.S. Provisional Patent Application Ser. No. 62/024,361, filed Jul. 14, 2014, which is owned by the assignee of the present application and is incorporated by reference in its entirety.

To describe the functionality of FIG. 3, the fluid travel will be described with respect to an aliquot of the working fluid 108. An aliquot of working fluid 108 flows from the working-fluid reservoir 102 to the first microchannel 24 of the OOC device 10 through input line 110 at a flow rate of $Q_1$. Once in the first microchannel 24, the aliquot travels from the input of the first microchannel 24 toward the output of the first microchannel 24 across the cells 34. While passing through the first microchannel 24, a first portion of the aliquot $Q_2$ will make it to the output of the first microchannel 24, and a second portion of the aliquot $Q_t$ will travel into the second microchannel 24 through the layer of cells 34 and barrier 30 (shown best in FIG. 3) due to the pressure gradient ΔP between the first microchannel 24 and the second microchannel 26. The first portion of the aliquot travels from the output of the first microchannel 24 to the first output-fluid reservoir 106a through output line 112a and the first fluid-resistance element 104a. The second portion of the aliquot travels from the output of the second microchannel 26 to the second output-fluid reservoir 106b through the output line 112b.

Once collected by the output-fluid reservoirs 106a and 106b, the first and the second aliquots can be compared as described above to determine the hydraulic conductivity of the cell layer 34 under dynamic operating conditions. In the illustrated embodiments, the flow rate of fluid collected by the second output-fluid reservoir 106b and fluid in the second microchannel 26 is entirely dependent on both the hydraulic conductivity of the barrier (the cell layer 34 and the barrier 30) and the pressure gradient between the two compartments because the fluid in the second microchannel 26 is only the fluid that has passed from the first microchannel 24 to the second microchannel 26 through the cell layer 34 and barrier 30. Beneficially, because the sum of the first output fluid 114a and the second output fluid 114b will equal the working fluid 108 input to the system, any two of the three values can be measured or known to determine the hydraulic conductivity of the barrier. For example, the hydraulic conductivity can be calculated when the working fluid 108 flow rate and the first output fluid 114a flow rate are measured or known, the working fluid 108 flow rate and the second output fluid 114b flow rate are measured or known, or when the first output fluid 114a flow rate and the second output fluid 114b are measured or known. It should be understood that the OOC device 10 can be placed in the system with only the barrier 30 (i.e. no cellular layer 34) to determine the hydraulic conductivity (or resistance) associated with only the barrier 30.

In some embodiments, a second flow-determining element is disposed in the fluid path of the second microchannel 26. This second flow-determining element provides for independent tuning of the flow rate through the first microchannel and the pressure gradient across the barrier 30 of the OOC device 10. Beneficially, use of the second flow-determining element provides for control of conditions in the second microchannel 26 and across the barrier 30 without altering the flow rate or other properties of the first microchannel 24. In some embodiments, the second flow-determining element is configured to control the flow rate through the second fluid path. In some embodiments, the second flow-determining element provides a backpressure to increase the pressure within the second microchannel 26, thereby reducing the pressure gradient across the barrier 30.

Figure 5:
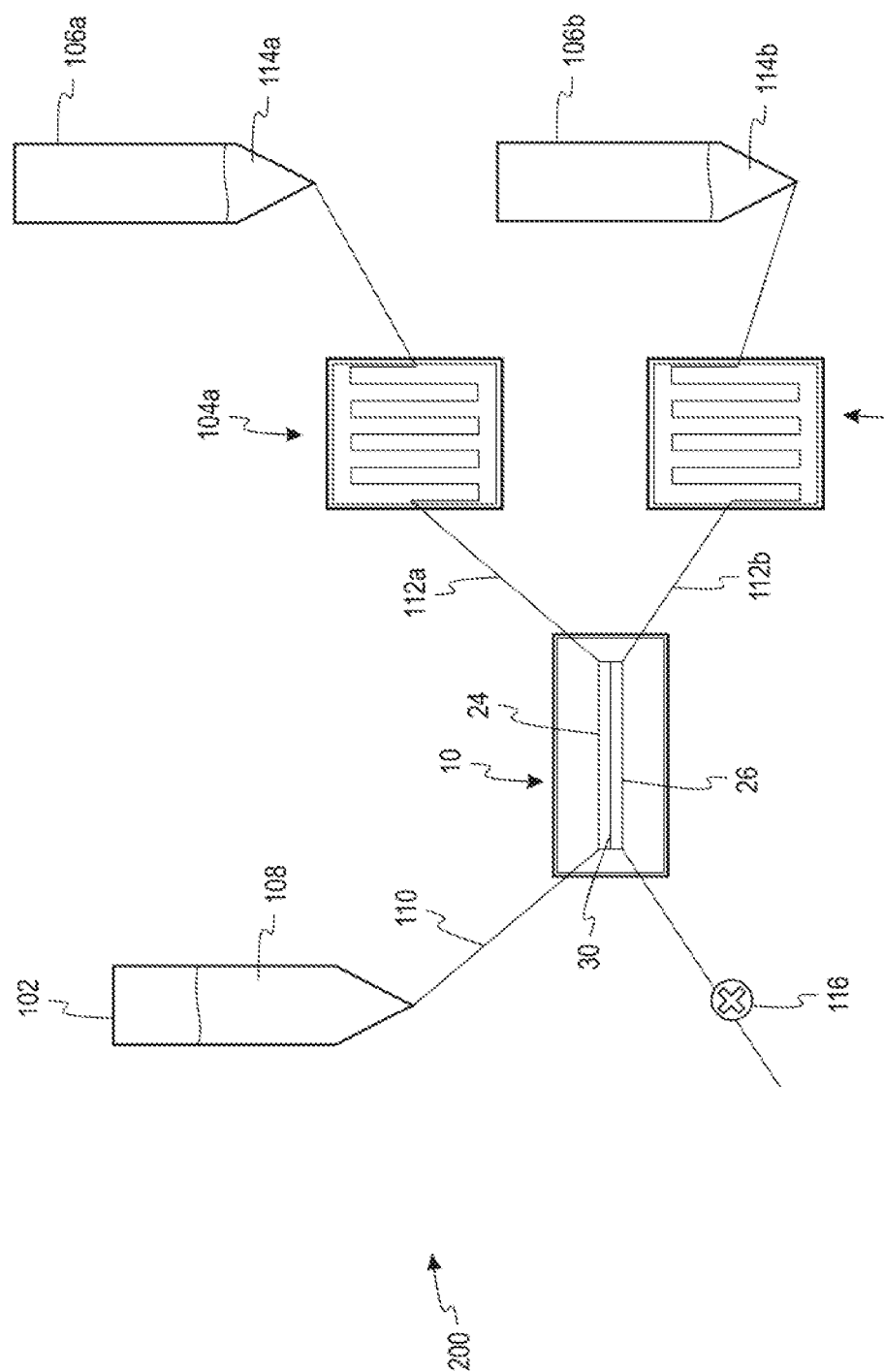
FIG. 5 illustrates a schematic representation of a system for quantifying the dynamic hydraulic conductivity of biological cell layers, according to further aspects of the present invention.

Referring now to FIG. 5, a schematic representation of a system 200 for quantifying the hydraulic conductivity of biological cell layers 34 is shown, according to aspects of the present invention. Like the system 100 of FIG. 4, the system 200 includes the working-fluid reservoir 102, the OOC device 10, the first flow-determining element such as the first fluid-resistance element 104a, the second flow-determining element such as the second fluid-resistance element 104b, the first output-fluid reservoir 106a, and the second output-fluid reservoir 106b. The working-fluid reservoir 102, the OOC device 10, the first fluid-resistance element 104a, the first output-fluid reservoir 106a, and the second output-fluid reservoir are the same as or similar to those described with respect to FIG. 4, above.

The second fluid-resistance element 104b is included in the flow path between the output of the second microchannel 26 and the second output-fluid reservoir 106b. The second fluid-resistance element 104b provides a backpressure to the fluid in the second microchannel 26 by providing predetermined fluidic resistance to the fluid path associated with the second microchannel 26. The fluidic resistance of the second fluid-resistance element 104b is generally lower than the fluidic resistance of the first fluid-resistance element 104a to allow for a pressure gradient ΔP across the cell layers 34 and the barrier 30. Beneficially, the second fluid-resistance element 104b can be used to alter the effective pressure gradient ΔP across the cell layers 34 and barrier 30 while the operating pressure and flow rate of the first microchannel 24 remain unaffected by the addition of the second fluid-resistance element 104b. Additionally, use of the second fluid-resistance element 104b provides for increased modularity of the system 200 because the first fluid-resistance element 104a can be selected to satisfy a first criterion, and the second fluid-resistance element 104b can be selected to satisfy a second criterion. For example, the first fluid-resistance element 104a can be selected to provide for a predetermined flow rate through the first microchannel 24, and the second fluid-resistance element 104b to provide for a predetermined pressure drop across the cell layers 34 and the barrier 30. As one skilled in the art will appreciate, the selection of the first fluid-resistance element 104a impacts selection of the second fluid-resistance element 104b and vice versa.

Flow through the system may be pressure driven or volume driven. In some embodiments, pressure-driven flow is accomplished by pressurizing the working-fluid reservoir 102 using, for example, a pressurized gas. In some embodiments, pressure-driven flow is accomplished using gravity by, for example, suspending the working-fluid reservoir 102 a distance above the remaining components of the system 100, 200. In some embodiments, volume-driven flow is accomplished using a volumetric pump supplying fluid to the system 100, 200 at a predetermined rate, for example, supplying fluid to the working-fluid reservoir 102 from an upstream process. In some embodiments, a volumetric pump may be integrated with the system 100, 200 and coupled to components such as the input line 110, or the first or second output lines 112a, 112b. Additionally, flow through the system or flow through components of the system can be determined, adjusted, and/or controlled using combinations of pressure-driven flow methods and volume-driven flow methods. For example, combinations of volumetric pumps, pressure-driven pumps, pressure regulators, flow-determining elements, and fluid-resistance elements can be employed to create desired conditions through each flow path and through the system as a whole.

To monitor fluid pressures in the system, any number of pressure sensors can be incorporated into the system 100, 200 to measure pressure at predetermined locations. For example, pressure sensors can be incorporated into fluid lines, reservoirs, the OOC device 10, the first and second microchannels 24, 26, or other suitable components.

In an example of the system 100 of FIG. 4, the OOC device 10 is a polydimethysiloxane ("PDMS") microfluidic device. The first and second microchannels 24, 26 have a length of 1.8 cm, a height of 100 and a width of 400 μm. The first and second microchannels 24, 26 are separated by a porous barrier 30 having a thickness of about 10 μm and pore sizes having a transverse dimension of about 10 μm. The cell layer 34 is formed from human umbilical vein endothelial cells that were grown in the first microchannel 24 until they reached confluence. The inlet of the first microchannel 24 was connected to a 25 cm raised working-fluid reservoir 102 with working fluid 108. The outlet of the first microchannel 24 was connected to a fluid-resistance element 104 having a length of about 1 cm, a height of about 60 μm, and a width of about 100 μm. The fluid-resistance element 104 provided a fluidic resistance that was more than 10 times higher than the resistance of the first microchannel 24 of the OOC device 10. In this example, the working fluid 108 exiting the working-fluid reservoir 102 had a pressure of about 25 cm $H_2O$, the fluid exiting the output of the first microchannel 24 of the OOC device 10 had a pressure of about 24.8 cm $H_2O$, and the fluid exiting the fluid-resistance element 104 had a pressure of about 0.1 cm $H_2O$.

In an example of the system 200 of FIG. 5, a second fluid-resistance element 104b was added to the above-described example system. In this example, the working fluid 108 exiting the working-fluid reservoir 102 had a pressure of about 25 cm $H_2O$. The fluid exiting the output of the first microchannel 24 of the OOC device 10 had a pressure of about 24.8 cm $H_2O$, the fluid exiting the first fluid-resistance element 104a had a pressure of about 0.1 cm $H_2O$, the fluid exiting the second microfluidic channel 26 had a pressure of about 10 cm $H_2O$, and the fluid exiting the second fluid-resistance element 104b had a pressure of about 0.1 cm $H_2O$.

Systems and methods in accordance with embodiments of the present invention can also be used to more accurately measure the dynamic permeability of biological layers. Permeability coefficients are the rate of diffusive (or in the case of bioactive molecules that are actively transported by tissues, quasi-diffusive) transport from one compartment to the other. The permeability coefficients are normalized for the steepness of the concentration gradient between the two compartments and for the surface area between the two compartments. The standard unit is generally expressed in terms of distance over time, such as m/s, cm/min, or cm/s. Because diffusive or quasi-diffusive transfer is generally much slower than convective transfer, even relatively small amounts of convective transfer can make it difficult, if not impossible, to accurately measure permeability coefficients.

In some embodiments for quantifying the dynamic permeability of biological cell layers, fluid is flowed through both the first and the second microchannels 24, 26. The fluid flowing through the first microchannel 24 is usually different from the fluid in the second microchannel 26. The fluids may be completely different compositions or may share one or more components. The pressure drop across the barrier and cell layer(s) is kept as close to zero as possible such that convective transfer is minimized and the transfer of compounds between the first microchannel and the second microchannel is due primarily to diffusive or quasi-diffusive transport through the cell layer. Fluidic resistance elements are disposed downstream of each microchannel of the microfluidic device to minimize the detrimental effects on flow and pressure within the microchannels, which may be caused by blockages such as small pieces of dirt, clumps of tissue, or small air bubbles that develop in the fluid path through the course of an experiment.

Figure 6:
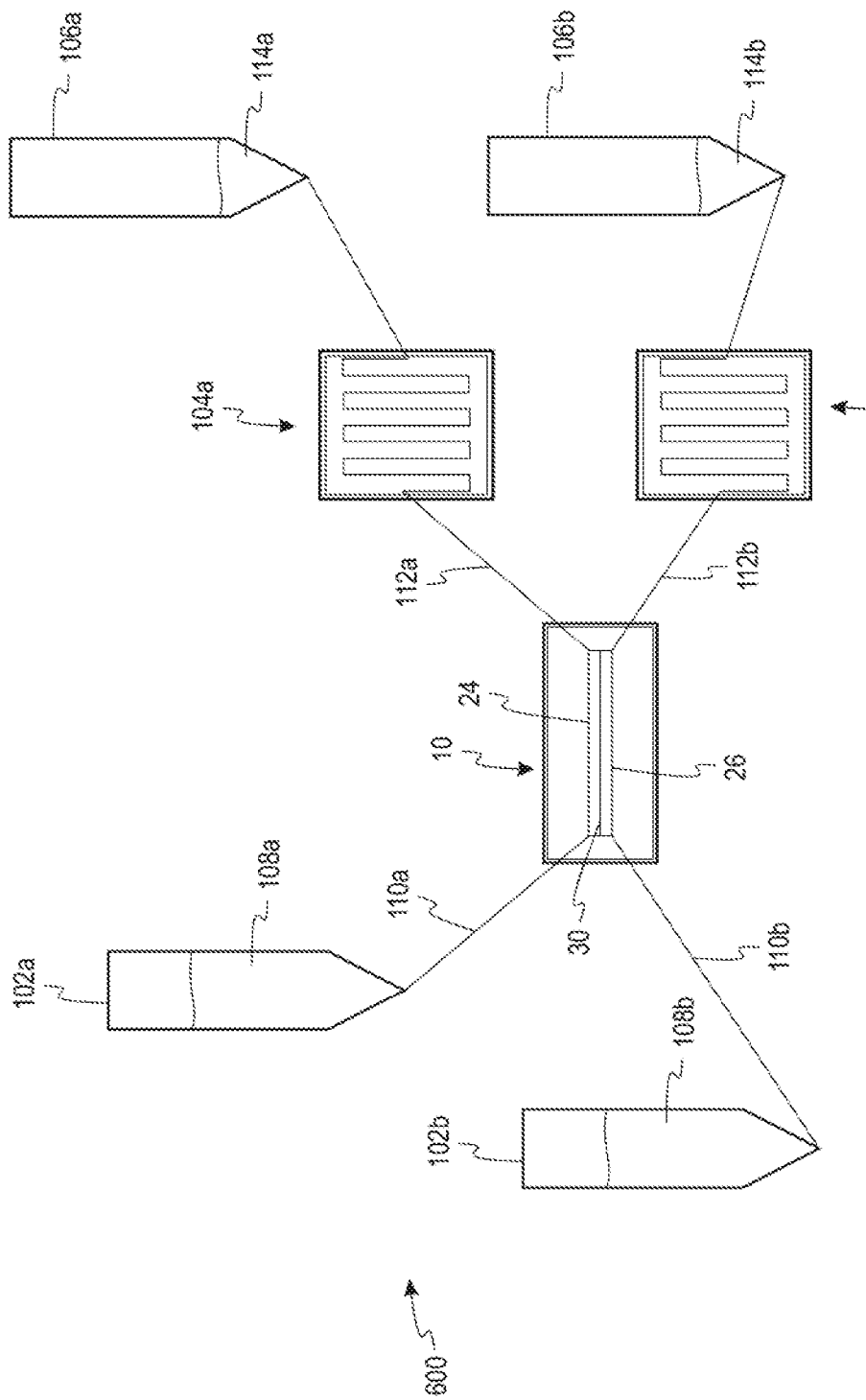
FIG. 6 illustrates a schematic representation of a system for quantifying the dynamic permeability of biological cell layers, according to aspects of the present invention.

FIG. 6 illustrates a schematic representation of a system 600 for quantifying the dynamic permeability of biological cell layers 34, according to aspects of the present invention. The system 600 includes a microfluidic device 10, a first working-fluid reservoir 102$a$, a first fluid-resistance element 104$a$, a first output-fluid reservoir 106$a$, a second working-fluid reservoir 102$b$, a second fluid-resistance element 104$b$, and a second output-fluid reservoir 106$b$. A first input line 110$a$ and a second input line 110$b$ fluidically couple the first working-fluid reservoir 102$a$ and the second working-fluid reservoir 102$b$ to the respective first microchannel 24 and second microchannel 26 of the microfluidic device 10. Output lines 112$a,b$ fluidically couple the first and the second microchannels 24, 26 to the respective first fluid-resistance element 104$a$ and second fluid-resistance element 104$b$, and the respective first and second output-fluid reservoir 106$a,b$. A first fluid path is defined by the first working fluid reservoir 102$a$, the first input line 110$a$, the first microchannel 24, the first output line 112$a$, the first fluid-resistance element 104$a$, and the first output-fluid reservoir 106$a$. Similarly, a second fluid path is defined by the second working fluid reservoir 102$b$, the second input line 110$b$, the second microchannel 26, the second output line 112$b$, the second fluid-resistance element 104$b$, and the second output-fluid reservoir 106$b$.

The first working-fluid reservoir 102$a$ includes a first working fluid 108$a$ therein that is flowed to the first output-fluid reservoir 106$a$ through the first fluid path. The second working-fluid reservoir 102$b$ includes a second working fluid 108$b$ therein that is flowed to the second output-fluid reservoir 106$b$ through the second fluid path. As the first working fluid 108$a$ or the second working fluid 108$b$ travels across the cell layer 34, one or more compounds are transferred between the first working fluid 108$a$ and the second working fluid 108$b$ to produce the first output fluid 114$a$ and the second output fluid 114$b$, respectively. Characteristics of one or both of the first and the second output fluids 114$a,b$ can be analyzed to determine the dynamic permeability through the barrier and the cell layer.

Figure 7:
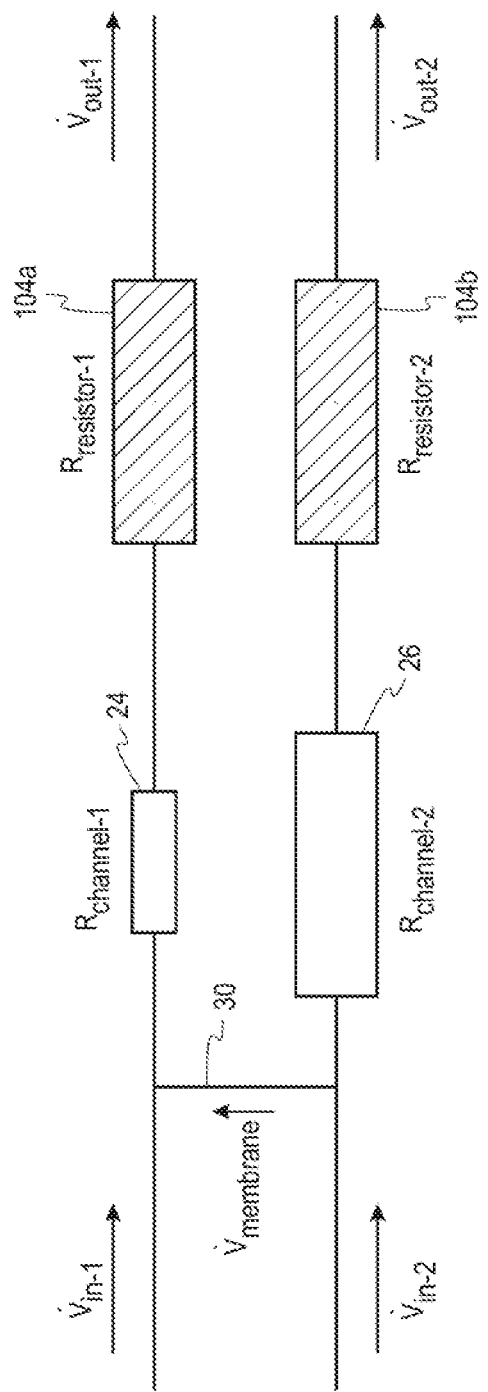
FIG. 7 illustrates a flow schematic of the system of FIG. 6.

FIG. 7 illustrates a flow schematic of the system of FIG. 6. The schematic includes the first channel 24, the second channel 26, the porous barrier 30, the first fluid-resistance element 104$a$, and the second fluid-resistance element 104$b$. The first microchannel 24 has a first nominal resistance $R_{channel-1}$, and the second channel 26 has a second nominal resistance $R_{channel-2}$. The nominal resistances $R_{channel-1}$, $R_{channel-2}$ are the resistances of the microchannels 24, 26 when no blockages are present. The first fluid-resistance element 104$a$ has a first fluidic resistance $R_{resistor-1}$, and the second fluid-resistance element 104$b$ has a second fluidic resistance $R_{resistor-2}$.

The first and second fluidic resistances $R_{resistor-1}$, $R_{resistor-2}$ are substantially larger than the nominal resistances $R_{channel-1}$, $R_{channel-2}$ of the respective microchannel 24, 26 to dampen or minimize the pressure differential across the barrier and associated cell layer(s). For example, in some embodiments, the first and second fluidic resistances $R_{resistor-1}$, $R_{resistor-2}$ are between about 10 times and about 40 times greater than the nominal fluid resistances $R_{channel-1}$, $R_{channel-2}$ of the respective microchannel 24, 26. In some embodiments, the first and second fluidic resistances $R_{resistor-1}$, $R_{resistor-2}$ are between about 40 times and about 100 times greater than the nominal fluid resistances $R_{channel-1}$, $R_{channel-2}$ of the respective microchannel 24, 26. In some embodiments, the first and second fluidic resistances $R_{resistor-1}$, $R_{resistor-2}$ are more than about 100 times greater than the nominal fluid resistances $R_{channel-1}$, $R_{channel-2}$ of the respective microchannel 24, 26. Because virtually all pressure in the system is needed to overcome the fluid-resistance elements 104$a,b$, the pressure distribution in the first and second microchannels 24, 26 is nearly uniform. This is true even if there are differences in nominal resistances $R_{channel-1}$, $R_{channel-2}$ of the microchannels 24, 26. Convective flow across the barrier 30 is minimized because pressure differences between the two microchannels 24, 26 are insignificant in the context of the entire system 600.

In summary, the difference in resistances between the fluid-resistance elements 104$a,b$ and the microchannels 24, 26 provides for a negligible pressure drop across the barrier 30 and inhibits convective transfer between the first and second working fluids 108$a,b$, even when a blockage occurs. The difference in resistances can also provide for a negligible pressure drop across the barrier 30 even when there are differences in the nominal resistances $R_{channel-1}$, $R_{channel-2}$ of the microchannels 24, 26.

By way of example, flow through systems with and without fluid-resistance elements 104$a,b$ will now be described and compared. In these examples, the nominal resistances $R_{channel-1}$, $R_{channel-2}$ of the microchannels are equal. The first input flow rate $J_{m-1}^{\&}$ and second input flow rate $J_{m-2}^{\&}$ are each 2 µL/min. Under ideal conditions with no pressure differential across the barrier, the convective flow rate $J_{membrane}^{\&}$ is 0 µL/min and the first output flow rate $J_{out-1}^{\&}$ and the second output flow rate $J_{out-2}^{\&}$ are each 2 µL/min. But under more realistic conditions, there is some pressure differential across the barrier because the resistances $R_{channel-1}$, $R_{channel-2}$ of the microchannels are different due to, for example, differences in flow channel geometry caused by differences in the geometry of the microchannel, present or size of tissue within the microchannel, or a minor obstruction such as small pieces of debris, clumps of tissue, or small air bubbles within the microchannel. For example, an accumulation of air bubbles can make the actual resistance of the second microchannel 26 four times its nominal resistance $R_{channel-2}$. This causes the resistance of the second fluid path to be four times the resistance of the first fluid path. The imbalance of resistances increases the pressure differential across the barrier 30 and increases the convective flow rate $J_{membrane}^{\&}$ across the barrier 30. In this example, the convective flow rate $J_{membrane}^{\&}$ increases from about 0 µL/min to about 1.2 µL/min. This convective transfer overwhelms any diffusive or quasi-diffusive transfer between the first and the second working fluids 108$a,b$ and causes inaccurate or incorrect characterization of the dynamic permeability of the cell layer 34.

To overcome the problems with diffusion measurements associated with increases in resistance (e.g., due to obstructions or different geometries), fluid-resistance elements 104a,b are added to each of the fluid paths. The addition of the fluid-resistance elements 104a,b significantly inhibits convective transfer between the first and second working fluids 108a,b by creating a larger pressure within each microchannel. In this example, the first and second fluidic resistances $R_{resistor-1}$, $R_{resistor-2}$ are 40 times the nominal resistances $R_{channel-1}$, $R_{channel-2}$ of the microchannels 24, 26. Thus, each of the unobstructed fluid paths has a total resistance of 41 times the nominal resistances $R_{channel-1}$, $R_{channel-2}$. Because the overall resistance of each fluid path is relatively high, an obstruction in either fluid path will have a much lower effect on the overall resistance of the fluid path. For example, an accumulation of air bubbles in the second microchannel 26 may make the actual resistance of the second microchannel 26 four times the nominal resistance $R_{channel-2}$, but the overall resistance of the fluid path would only be about 10% greater than the resistance of the first fluid path (e.g., 45 times the nominal resistances $R_{channel-1}$, $R_{channel-2}$). This dampens the increased pressure differential across the barrier 30 and inhibits convective flow across the barrier 30 and associated cell layer(s) 34. In this example, the convective flow rate $J_{membrane}^{\&}$ increases from about 0 μL/min to only about 0.07 μL/min. Because the convective transfer remains low, diffusive or quasi-diffusive transfer between the first and the second working fluids 108a,b can still be measured. Beneficially, any convective transfer that does occur across the barrier 30 and cell layer(s) 34 can be accounted for because the flow rates of the first and second working fluid 108a,b into the system are generally known, and the convective flow is low enough so as to not overwhelm the measurements. In some embodiments, the increased accuracy is achieved by subtracting any analyte transported through convective transfer from the measured amount of analyte. This further increases the accuracy of characterizing the dynamic permeability of the cell layer(s) 34 within the system. Additionally, the accuracy of the measured permeability can be increased by removing the effects of known components known components such as the barrier 30 or additional cell layers 34. More specifically, the measured permeability can be corrected using the following equation:

$$P_{Layer} = P_{Total} - \frac{1}{\frac{1}{P_{Total}} - \frac{1}{P_{Knowns}}}$$

Where $P_{Total}$ is the measured permeability, $P_{Knowns}$ is the permeability of known components such as the barrier and known layers, and $P_{Layer}$ is the permeability of the unknown layer or layers.

While the microchannels 24, 26 of the above-described systems 100, 200, 600 have had a backpressure applied by fluid-resistance elements 104, the output-fluid reservoirs 106a, 106b can be used to provide, supplement, or adjust the backpressure applied to the microchannels 24, 26. For example, in system 200, the second fluid-resistance element 104b providing about 10 cm $H_2O$ backpressure. This 10 cm $H_2O$ backpressure can alternatively be provided by removing the second fluid-resistance element 104b, and raising the second output-fluid reservoir 106b by 10 centimeters from its original position. In yet another alternative, the second fluid-resistance element 104b can provide 5 cm $H_2O$ backpressure, and the second output-fluid reservoir 106b can be raised 5 centimeters from its original position to supplement the backpressure provided by the second fluid-resistance element 104b, thus providing a total backpressure of 10 cm $H_2O$.

While the above-described systems 100, 200, 600 have been described as employing an OOC device 10 having two microchannels 24, 26, it is contemplated that OOC devices 10 having three or more microchannels. Barriers 30 are disposed between adjacent microchannels of the OOC device 10 to allow for diffusion between the adjacent microchannels. Depending on the application, the barrier 30 may have a porosity to permit the migration of cells, particulates, media, proteins, and/or chemicals between the adjacent microchannels. Moreover, the barriers may have different porosities. For example, a barrier between a first and a second microchannel may have a different porosity than a barrier between the second and a third microchannel. The microchannels may be arranged in any suitable fashion. In some embodiments, a high-pressure channel is disposed between two lower pressure channels. In some embodiments, a high-pressure channel is disposed adjacent a moderate-pressure channel, which is disposed adjacent a low-pressure channel in a "cascading fashion." It is contemplated that various combinations of pressures and cell layers may be used on OOC devices 10 having three or more microchannels to provide in-vitro modeling of a variety of conditions that are otherwise impractical or impossible to replicate (e.g., exploration of how various backpressures affect transfer through complex systems, differences in selective permeation between a first cell layer and a second cell layer, etc.).

While the above-described systems 100, 200, 600 have been discussed with respect to the fluid-resistance elements 104 and output-fluid reservoirs 106a, 106b providing a constant backpressure, the systems 100, 200 can have a dynamic fluidic resistance that varies or is selectively varied over time. For example, the fluidic resistance provided by the fluid-resistance elements can be a dynamic fluidic resistance using an air-filled tube that is sealed. In this example, the fluid would compress the air in the tube and the backpressure would increase until the pressure of air approximately matches the pressure in the respective microchannel. As the backpressure increases, flow through the respective microchannel would decrease, creating dynamic fluctuations in the system that can be used to more accurately simulate conditions in-vivo. The air-filled tube can be included in, for example, the first fluid-resistance element 104a, the second fluid-resistance element 104b, or both. In another example, backpressure is provided by an air-filled tube that is open and extends to a predetermined height. This predetermined height can correspond to a maximum desired backpressure, or to a point that is higher than pressure on the remainder of the system. In this example, the fluid would fill the air-filled tube and the backpressure would increase based on the height of the fluid in the tube. Moreover, it is contemplated that fluid-resistance elements 104 can be adjusted or altered to increase or decrease fluidic resistance.

While the above-described systems 100, 200, 600 have been discussed with respect to the fluid-resistance elements 104 being disposed downstream of the microfluidic device 10, it is contemplated that embodiments of the present invention may include fluid-resistance elements 104 being disposed upstream of the microfluidic device 10. Further, while embodiments of the above-described systems 600 have been discussed with respect to measuring dynamic permeability, it is contemplated that systems and methods in accord with the present disclosure may be used to measure more general permeability of the cell layers.

Microfluidic devices for cell culture typically need to be perfused with fluid media at an extremely low flow rate, such as between 30 μL/hr and 5 mL/hr. Moreover, in some experiments, these flow rates must be consistent for several weeks. According to existing approaches for device interconnection, fluidic (microfluidic and/or non-microfluidic) devices are typically interconnected using tubing and valves that connect the output of one device to the input of another. However, the use of tubing and valves presents some disadvantages, such as the need to limit accumulation of media within the system over the course of the experiment. Beneficially, the use of fluid-resistance elements also allows for systems in accord with the present invention to be incorporated into larger systems regardless of the operating conditions of the larger system as flow rates and other properties can be selected and controlled to fit the required operating conditions of the specific system while maintaining a desired operating pressures across the microchannels 24, 26, operating pressure gradient ΔP across the barrier 30, and flow rates $J_{m-1}^{\&}$, $J_{m-2}^{\&}$, $J_{out-1}^{\&}$, $J_{out-2}^{\&}$ through the system.

Figure 8:
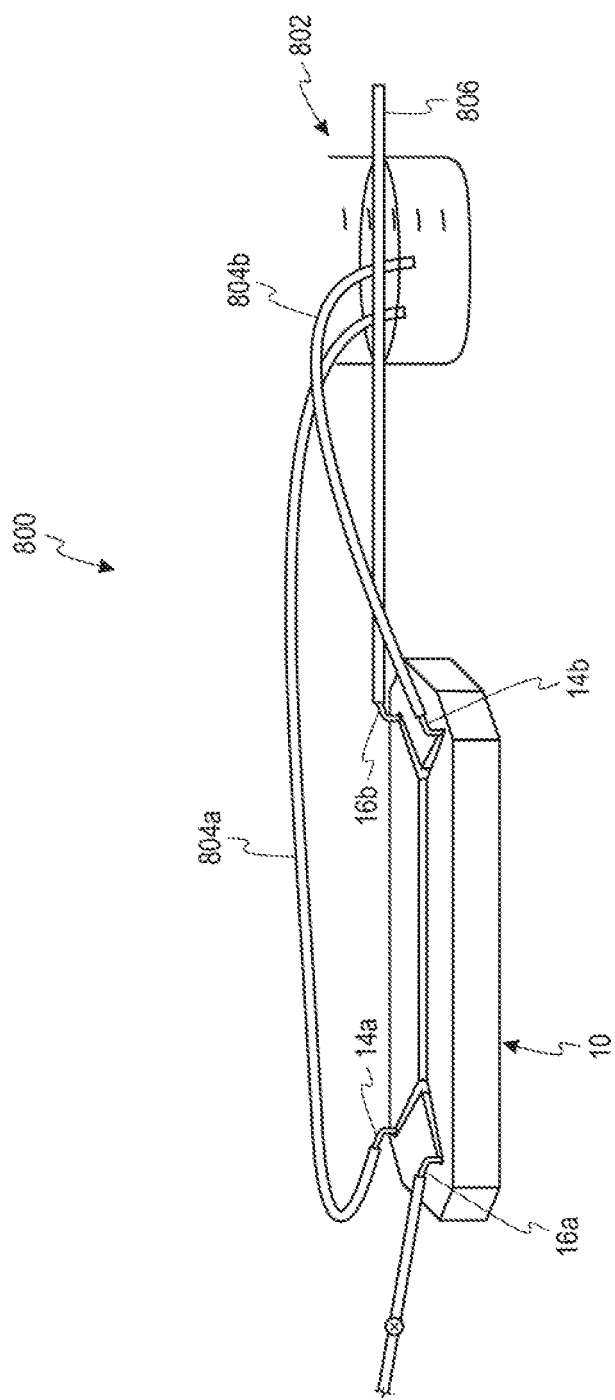
FIG. 8 illustrates a schematic representation of a system for quantifying fluid transport across biological cell layers, according to aspects of the present invention.

Referring now to FIG. 8, a representation of a system 800 for quantifying fluid transport across biological cell layers is shown according to aspects of the present invention. The system 800 includes a working-fluid reservoir 802 and an OOC device 10. As shown best in FIG. 1, the OOC device 10 includes a first fluid inlet 14a, a first fluid outlet 14b, a second fluid inlet 16a, and a second fluid outlet 16b. A first fluid line 804a extends between the first fluid inlet 14a and the working-fluid reservoir 802. A second fluid line 804b extends between the first fluid outlet 14b and the working-fluid reservoir 802. The second fluid inlet 16a is plugged such that fluid does not generally flow through the second fluid inlet 16a. A third fluid line 806 extends from the second fluid outlet 16b.

When in use, the first fluid line 804a, the first microchannel 24, the second fluid line 804b, and the working-fluid reservoir 802 form a first fluid path. The fluid path is loaded with working fluid contained in the working-fluid reservoir 802 such that any movement of fluid from the first microchannel 24 to the second microchannel 26 draws working fluid from the working-fluid reservoir toward the first microchannel 24. The third fluid line 806 is suspended at generally the same height as the level of working fluid in the working fluid reservoir 802 such that the pressure gradient across the barrier 30 is generally zero. In this way, mass transfer of the working fluid across the barrier 30, such as pressure-driven flow, is inhibited. Accordingly, hydrostatic head pressure is eliminated such that fluid flow from the first microchannel to the second microchannel is due to the cell layer. For example, pumping activity of cells within the cell layer will transport working fluid from the first microchannel 24 to the second microchannel 26. This flow can be monitored by measuring fluid flow through the third fluid line 806. A marker within the third fluid line 806 can be used to measure fluid flow by, for example, monitoring displacement of the marker over time. The marker can include, for example, the leading edge of the working fluid or a gas bubble within the third fluid line. Additionally or alternatively, the weight or volume of the working fluid within the third fluid line 806 can be measured to determine the flow rate of working fluid across the membrane.

For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." Additionally, the singular terms "a," "an," and "the" include plural referents unless context clearly indicates otherwise.

While the above detailed description has described particular embodiments with reference to microfluidic components, it is contemplated that the above-described concepts are applicable to larger systems. These larger systems include, for example, millifluidic and fluidic systems.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A method for measuring dynamic hydraulic conductivity, comprising:
   providing a microfluidic device comprising a first microchannel and a second microchannel separated by a barrier, said first microchannel having a first outlet, and said second microchannel having a second outlet, wherein a cell layer is disposed on said barrier;
   flowing a working fluid through said first microchannel at a flow rate, said working fluid at a first pressure at said barrier;
   collecting a first portion of said working fluid at said first outlet and a second portion of said working fluid that has migrated through said cell layer at said second outlet; and
   determining the dynamic hydraulic conductivity of cells in the cell layer.

2. The method of claim 1, wherein said barrier further comprises a first side and a second side, and said layer of cells are disposed on at least one of said first side and second side.

3. The method of claim 1, wherein said flow rate causes a shear stress on the cell layer.

4. The method of claim 1, wherein the dynamic hydraulic conductivity of the cells in the cell layer is determined by performing an image-gathering technique on the layer of cells during the flowing of a working fluid step.

5. The method of claim 1, wherein the dynamic hydraulic conductivity of the cells in the cell layer is determined based on the volume of at least one of said first portion and said second portion of said working fluid.

6. The method of claim 1, further comprising monitoring a marker associated with the fluid that travels through the layer of cells and the barrier and that exits the second microchannel.

7. The method of claim 1, wherein said determining is based on said first pressure and said collected second portion of said working fluid exiting the second microchannel.

8. The method of claim 1, wherein said second portion of said working fluid has migrated due to active transport.

9. The method of claim 8, wherein pressure is applied while flowing said working fluid through said first microchannel.

10. A method for measuring dynamic hydraulic conductivity, comprising:
    a) providing a microfluidic device comprising a first microchannel and a second microchannel separated by a barrier, said first microchannel having a first outlet, and said second microchannel having a second outlet, wherein a cell layer is disposed on said barrier;

b) applying a first working fluid to said first microchannel;
c) applying a second working fluid to said second microchannel;
d) collecting a first portion of said first working fluid at said first outlet and a second portion of said first working fluid that has migrated due to active transport through said cell layer at said second outlet; and
e) determining the dynamic hydraulic conductivity of cells in the cell layer.

11. The method of claim 10, wherein said barrier further comprises a first side and a second side, and said layer of cells are disposed on at least one of said first side and second side.

12. The method of claim 10, wherein said application of said first working fluid and said second working fluid causes a shear stress on the cell layer.

* * * * *